(12) United States Patent
Nakayama et al.

(10) Patent No.: US 8,575,117 B2
(45) Date of Patent: Nov. 5, 2013

(54) PROLIFERATION INHIBITOR OF HELICOBACTER PYLORI INCLUDING ALPHA-N-ACETYL-GLUCOSAMINYL BOND-CONTAINING MONOSACCHARIDE DERIVATIVES

(75) Inventors: Jun Nakayama, Matsumoto (JP); Takashi Yamanoi, Tokyo (JP); Masaya Fujita, Tokyo (JP); Takashi Shirai, Tokyo (JP)

(73) Assignee: The Noguchi Institute, Tokyo (JP)

( * ) Notice: Subject to any disclaimer, the term of this patent is extended or adjusted under 35 U.S.C. 154(b) by 164 days.

(21) Appl. No.: 12/662,309

(22) Filed: Apr. 9, 2010

(65) Prior Publication Data

US 2010/0197616 A1  Aug. 5, 2010

Related U.S. Application Data

(63) Continuation of application No. 11/664,437, filed as application No. PCT/JP2007/050741 on Jan. 12, 2007, now abandoned.

(51) Int. Cl.
*A61K 31/7008* (2006.01)
*A61K 31/7034* (2006.01)

(52) U.S. Cl.
USPC .............................................. 514/35; 514/25

(58) Field of Classification Search
None
See application file for complete search history.

(56) References Cited

U.S. PATENT DOCUMENTS

| 2,710,807 A | 6/1955 | Gyorgy et al. |
| 4,152,513 A | 5/1979 | Austin et al. |
| 6,756,489 B1 | 6/2004 | Schmidt et al. |
| 2004/0086514 A1 | 5/2004 | Karlsson et al. |
| 2009/0054355 A1 | 2/2009 | Nakayama et al. |
| 2011/0237788 A1 | 9/2011 | Nakayama et al. |

FOREIGN PATENT DOCUMENTS

| JP | A-2001-512737 | 8/2001 |
| JP | A 2003-517015 | 5/2003 |
| JP | A-2007-246426 | 9/2007 |
| WO | WO 94/03184 A1 | 2/1994 |
| WO | WO 99/07718 | 2/1999 |
| WO | WO 01/43751 A1 | 6/2001 |
| WO | WO 2005/081904 A2 | 9/2005 |
| WO | WO 2008/032817 A1 | 3/2008 |
| WO | WO 2008/084561 A1 | 7/2008 |

OTHER PUBLICATIONS

Mayo Clinic Staff "H. pylori infection", also available at http://www.mayoclinic.com/health/h-pylori/DS00958; last viewed Sep. 28, 2010.*

Adolfsson, O. et al., The American Journal of Clinical Nutrition, "Yogurt and gut function", 2004, vol. 80, pp. 245-256.*

Suerbaum, S. et al., The New England Journal of Medicine, "Medical Progress: *Helicobacter pylori* Infection", 2002, vol. 347, No. 15, pp. 1175-1186.*

Wood, A. J. J., The New England Journal of Medicine, "Drug Therapy: The Treatment of *Helicobacter pylori* Infection in the Management of Peptic Ulcer Disease", 1995, vol. 333, No. 15, pp. 984-991.*

B. Marshall et al., "Unidentified Curved Bacilli in the Stomach of Patients with Gastritis and Peptic Ulceration", The Lancet Jun. 1984, pp. 1311-1314.

R. Peek Jr. et al., "*Helicobacter pylori* and Gastrointestinal Tract Adenocarcinomas", Nature Reviews: Cancer, Jan. 2002 vol. 2, pp. 28-37.

M. Kawakubo et al., "Natural Antibiotic Function of a Human Gastric Mucin Against *Helicobacter pylori* Infection", Science Aug. 2004, vol. 305, No. 5686, pp. 1003-1006.

Y. Hirai et al., "Unique Cholesteryl Glucosides in *Helicobacter pylori*: Composition and Structural Analysis", Journal of Bacteriology, Sep. 1995, vol. 177, No. 18, pp. 5327-5333.

Merriam-Webster Online Dictionary "derivative", available at http://www.merrima-webster.com/dictionary/derivate, last viewed Aug. 6, 2009.

S. Ebisu et al, Equilibrium Dialysis and Carbohydrate-Building Studies on the 2-Deoxy-D-Glucopyranosyl Binding Lectin from Bandeiraea simplicifolia Seeds, Carbohydrate Research vol. 16, 1978 pp. 129-138.

A. Neuberger et al. "Inhibion of Lysozyme by Derivatives of D-Glucosamine. I." Biochim. Biophys. Acta. Vaol 147, 167 pp. 473-486.

J. Goto et al., Synthesis of Conjugated Cholestrol and Cholestrolas,Chem. Pharm Bull, vol. 27—No. 8, 1979, pp. 1926-1931.

International Search Report for Application No. PCT/JP2007/050741; mailed Mar. 20, 2007.

(Continued)

*Primary Examiner* — Layla Bland
*Assistant Examiner* — Bahar Craigo
(74) *Attorney, Agent, or Firm* — Oliff & Berridge, PLC

(57) ABSTRACT

A method for inhibiting proliferation of *Helicobacter pylori* including a compound that can simply be mass-produced, can specifically inhibit the proliferation of *H. pylori*, which has high safety and never generates any resistant bacteria, as well as a diet of a food or beverage, and a pharmaceutical preparation containing the proliferation inhibitor of *Helicobacter pylori*. The proliferation inhibitor of *Helicobacter pylori* comprises an alpha-N-acetyl-glucosaminyl bond-containing monosaccharide derivative represented by the following chemical formula (1)

GlcNAc1-alpha-O—Y        (1)

(in the formula (1), Y is a straight-, branched- or cyclic-aliphatic hydrocarbon group having 1 to 27 carbon atoms or a straight-, branched- or cyclic-acyl group having 1 to 27 carbon atoms). The diet of the food, the beverage or the pharmaceutical preparation comprises the proliferation inhibitor of *Helicobacter pylori*.

2 Claims, 2 Drawing Sheets

(56) References Cited

OTHER PUBLICATIONS

Oct. 28, 2010 European Search Report issued in Application No. 07710493.3.

Hoshino et al., "Search for Aryl N-Acetyl-A-D-Glucosaminides which Suppress the Growth of *Helicobacter pylori*," Meeting of the Society for Gylcobiology, Universal City, CA, U.S.A., Nov. 15-19, 2006, Oxford University Press, vol. 16, No. 11, p. 1145, Nov. 1, 2006, XP008127483.

Fukuda et al., "Assay of Human Gastric Mucin as a Natural Antibiotic Against *Helicobacter pylori*," Methods in Enzymology, vol. 415, pp. 164-179, Jan. 1, 2006, XP008127473.

Miller-Podraza et al. "Novel Binding Epitope for *Helicobacter pylori* Found in Neolacto Carbohydrate Chains," *The Journal of Biological Chemistry*, vol. 280, No. 20, 2005, pp. 19695-19703.

Iwahara et al. "Isolation and Identification of Ethyl-β-Acetylglucosaminide from Yeast Extract," *Biosci. Biotech. Biochem.*, vol. 57, No. 10, 1993, pp. 1779-1780.

Nagai, "Clinical and Experimental Studies on Ethyl-N-Acetyl-D-Glucosamine as Bifidus Factor," Paediatria Japonica, Japanese Paediatric Society, vol. 3, No. 6, pp. 83-102, Nov. 1960.

U.S. Appl. No. 13/063,876, filed Jun. 9, 2011, Jun Nakayama et al.

U.S. Appl. No. 13/737,609, filed Jan. 9, 2013, Jun Nakayama et al.

Oct. 9, 2012 Office Action issued in U.S. Appl. No. 13/063,876.

\* cited by examiner

H.Pylori-Resistant Effect of Compound 2

PROLIFERATION INHIBITOR OF HELICOBACTER PYLORI INCLUDING ALPHA-N-ACETYL-GLUCOSAMINYL BOND-CONTAINING MONOSACCHARIDE DERIVATIVES

This is a Continuation of application Ser. No. 11/664,437 filed Jun. 20, 2007. The disclosure of the prior application is hereby incorporated by reference in its entirety.

The present invention relates to a proliferation inhibitor comprising an alpha-N-acetyl-glucosaminyl bond-containing monosaccharide derivative, which can inhibit the proliferation of *Helicobacter pylori* (*H. pylori*) as a causative microorganism for diseases such as peptic ulcers and gastric cancers.

BACKGROUND ART

*Helicobacter pylori* (*H. pylori*) is a gram-negative bacterium belonging to the genus *Spirillum* isolated from the gastric mucous membrane of a patient suffering from chronic gastritis and cultivated (Marshall B. J., Warren J. R., Lancet, 1984, 1:1311-1315). It has already been elucidated that such *H. pylori* is closely related not only to the crises of chronic gastritis and peptic ulcers, but also to the crises of serious or advanced gastric disease such as gastric cancers and gastric malignant lymphoma (Peek R. M. Jr., Blaser M. J., Nature. Rev. Cancer, 2002, 2:28-37).

It has been said that the total number of the persons infected with *H. pylori* would reach almost a half of the total population in all of the world, but these gastric diseases are not always advanced even to serious conditions thereof in all of the infected persons. This fact clearly indicates that the gastric mucous membrane in itself would be provided with the mechanism of protecting the same from the infection of the bacterium, *H. pylori*.

*H. pylori* inhabits in the superficial mucus secreted from the surface layer of the gastric mucous, but never inhabits in the mucous and the glandular mucus secreted from the mucous deep layer. This glandular mucus inherently contains a sugar chain derived from O-glycan having an alpha-N-acetyl-glucosaminyl residue (alpha GlcNAc residue) at the terminal thereof. For this reason, the foregoing fact would suggest that the sugar chain may protect the gastric mucous from the infection with *H. pylori*.

An article of Kawakubo M. et al., Science, 2004, 305:1003-1006 discloses the effect of alpha GlcNAc residue on the proliferation of *H. pylori*. This article likewise discloses that glycoproteins which are each linked with a core binary-branched O-glycan having an alpha GlcNAc bond at the un-reduced terminal (GlcNAc alpha 1-4Gal beta 1-4GlcNAc beta 1-6(GlcNAc alpha 1-4Gal beta 1-3)GalNAc-R) can substantially inhibit the proliferation and mobility of *H. pylori* and can likewise induce considerable changes such as the elongation of bacterial cells and the formation of asymmetric contours and the fragmentation thereof. A series of these changes are not observed at all in case of the O-glycan free of any alpha GlcNAc residue. In addition, this article also states that the glycosyl cholesterol components (CGL) which exist in the surface layer of the bacterial cells are significantly reduced, as has been deduced from the results obtained by the morphological observation of *H. pylori* in the presence of sugar chains each carrying the foregoing alpha GlcNAc residue.

*H. pylori* essentially requires CGL for the survival thereof, but it cannot synthesize the same by itself (Hirai Y. et al., J. Bacteriol., 1995, 177:5327-5333). Accordingly, it would be believed that *H. pylori* takes in cholesterols from the external world and adds glucose to the region in the proximity to the membrane of the bacterial cell to thus construct the cell wall. In this respect, it would thus be estimated that the foregoing sugar chain carrying the alpha GlcNAc residue has an ability to inhibit the construction of such a cell wall. However, it requires the use of multiple steps and great expense to chemically or enzymatically synthesize the foregoing core binary-branched O-glycan having an alpha GlcNAc bond at the un-reduced terminal and therefore, the chemical or enzymatic synthesis of the O-glycan is not considered to be practicable.

Moreover, Japanese Patent Provisional Publication No. 2003-517015 discloses substances having an ability of being linked with *H. pylori*, which have sugar chains each including smaller Gal beta 3GlcNAc or Gal beta 3GalNAc, but a method for the preparation of these substances is quite complicated and therefore, the method never permits the mass production of the same.

On the other hand, the presently used methods for treating patients infected with *H. pylori* are not ones which make use of these sugar chains, but they mainly comprise the step of exterminating bacterial cells through the simultaneous use of the following three kinds of drugs: a kind of proton pump-inhibitor and two kinds of antibiotics. In the medical treatment with which the three kinds of drugs are combined, problems further arise such that this treatment may induce the generation of resistant bacteria to thus cause the recurrence of the infectious disease and that they may cause side effects.

For this reason, there has been desired for the development of a proliferation inhibitor of *H. pylori* comprising alpha GlcNAc residue-containing sugar chain derivative, which never exerts any adverse effect on the human body such as a side effect, can be produced in commercial quantity and can easily be prepared.

SUMMARY OF THE INVENTION

The present invention has been developed to solve the foregoing problems. It is an object of the present invention to provide a proliferation inhibitor of *H. pylori* comprising a compound that can simply be mass-produced, can specifically inhibit the proliferation of *H. pylori*, which has high safety and never generates any resistant bacteria, as well as a diet of a food or beverage and a pharmaceutical preparation containing the proliferation inhibitor.

According to the present invention, the proliferation inhibitor of *H. pylori* developed for the achievement of the foregoing object, comprises an alpha-N-acetyl-glucosaminyl bond-containing monosaccharide derivative represented by the following chemical formula (1):

GlcNAc1-alpha-O—Y    (1)

(In Formula (1), Y is a straight-, branched- or cyclic-aliphatic hydrocarbon group having 1 to 27 carbon atoms; or a straight-, branched- or cyclic-acyl group having 1 to 27 carbon atoms).

In addition, the diet of the food or the beverage developed for the achievement of the foregoing object, comprises the foregoing proliferation inhibitor of *H. pylori*.

Moreover, the pharmaceutical preparation developed for the achievement of the foregoing object, comprises the foregoing proliferation inhibitor of *H. pylori*.

The alpha-N-acetyl-glucosaminyl bond-containing monosaccharide derivative possesses an anti-bacterial effect to thus inhibit the proliferation of *H. pylori*. When using this sugar derivative, there is not any possibility of generating any resistant bacteria unlike the administration of the antibiotics.

The sugar derivative can simply be produced and is quite suitable for the industrial production in commercial quantity.

According to the sugar derivative-containing pharmaceutical preparation, the sugar derivative inhibits the construction of the cell wall of *H. pylori* to thus specifically inhibit the proliferation of the bacteria and therefore, it can show a drug efficacy against *H. pylori*. In addition, the proliferation inhibitor of *H. pylori* can be used alone or in combination with other drugs such as antibiotics to thus completely remove *H. pylori* from the stomach and to prevent the recurrence of gastric diseases such as chronic gastritis, peptic ulcers, gastric cancers and/or gastric malignant lymphoma. Furthermore, in the structure of the sugar derivative, the aglycon site thereof is composed of non-toxic groups such as an aliphatic hydrocarbon group typical of a lower or higher saturated or unsaturated alkyl group or a cholestanyl group, or an acyl group, and accordingly, the proliferation inhibitor of *H. pylori* would have quite high safety to the human body.

The diet of the food or the beverage each containing the proliferation inhibitor of *H. pylori* is useful for alleviating the symptoms of gastric diseases and/or the prevention of such diseases. This sugar derivative shows a strong action of inhibiting the proliferation of *H. pylori*. Consequently, if the sugar derivative is simply incorporated into the diet of these foods and beverages in a small quantity, the resulting diet of the foods and the beverages can show excellent *H. pylori*-resistant effects.

Moreover, the pharmaceutical preparation comprising the proliferation inhibitor of *H. pylori* is effective for curing gastric diseases caused by the *H. pylori* such as chronic gastritis and gastric ulcers. The sugar derivative shows a strong effect of inhibiting the proliferation of *H. pylori* and therefore, an excellent *H. pylori*-resistant effect can be anticipated simply by taking a small amount of this pharmaceutical preparation and accordingly, the latter is useful for the medical treatment of gastric diseases, the alleviation of the symptoms thereof and/or the prevention of the same.

MODES FOR CARRYING OUT THE INVENTION

Figure 1:
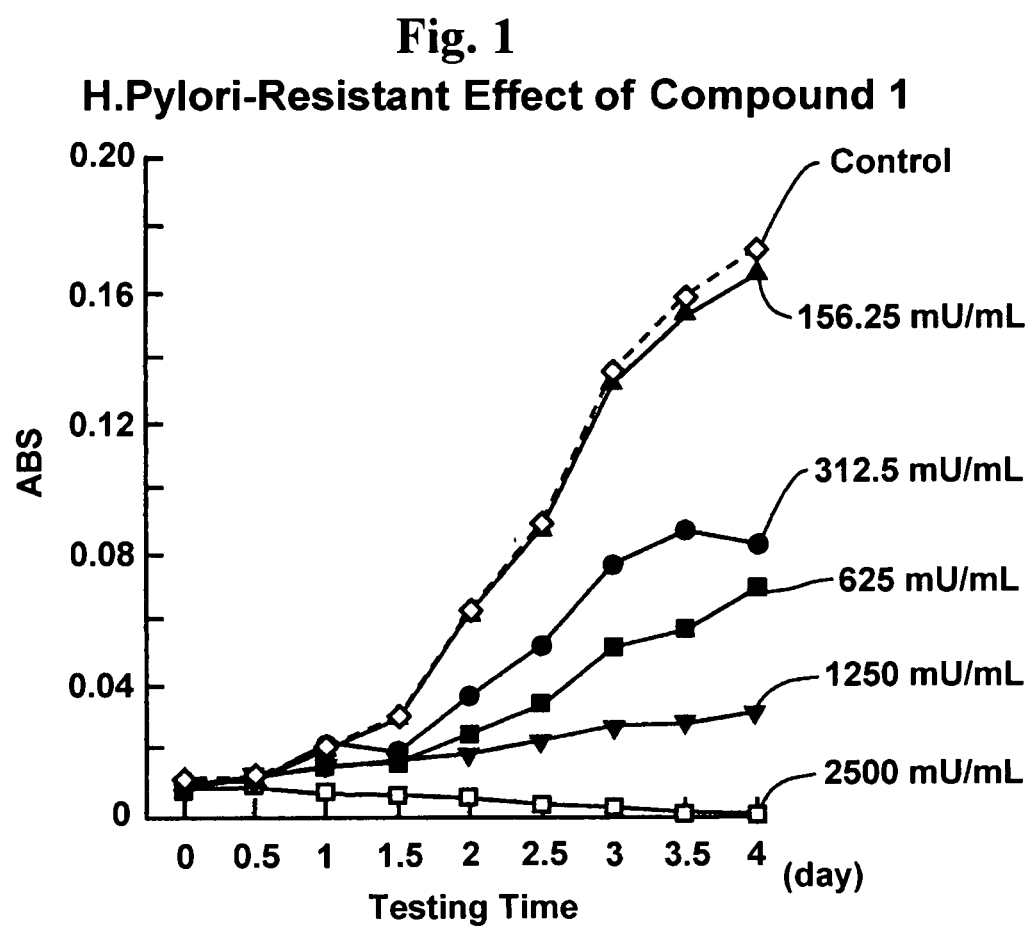
FIG. 1 is a graph showing the *H. pylori*-resistant effect of a proliferation inhibitor of *H. pylori* comprising alpha-N-acetyl-glucosaminyl bond-containing monosaccharide derivative (Compound 1) to which the present invention is applied.

Embodiments according to the present invention will hereunder be described in detail, but the present invention is, by no means, limited to these specific embodiments at all.

The alpha-N-acetyl-glucosaminyl bond-containing monosaccharide derivative included in the proliferation inhibitor of *H. pylori* of the present invention is represented by the foregoing chemical formula (1), or GlcNAc1-alpha-O—Y, wherein Y is an aliphatic hydrocarbon group such as an alkyl group. More specifically, the derivative has such a structure that an N-acetyl-glucosaminyl group (GlcNAc) is linked at the alpha-position.

The alpha-N-acetyl-glucosaminyl bond-containing monosaccharide derivative has an excellent effect of inhibiting the proliferation of *H. pylori*. For instance, when a culture medium containing a monosaccharide derivative carrying an ethyl group (GlcNAc-alpha-O-Et) in a concentration of not less than 1.8 mM is coexistent with *H. pylori*, the monosaccharide derivative can control the proliferation ability of *H. pylori* to a level of not more than 50%. In particular, such a culture medium containing the monosaccharide derivative in a concentration of not less than 7.2 mM can completely inhibit the proliferation of *H. pylori*. This monosaccharide derivative is never decomposed within not only the culture mediums, but also the stomach. This alpha-N-acetyl-glucosaminyl bond-containing monosaccharide derivative (GlcNAc-alpha-O-Et) is not only a monosaccharide, but also a compound simply prepared through a single-step synthetic method and accordingly, it can be produced in commercial quantity or scale. In addition, this monosaccharide derivative is quite stable since it is an aliphatic hydrocarbon group-substituted derivative of N-acetylglucosamine and the substituent is linked to the glucosamine through an ether bond. Moreover, the aliphatic hydrocarbon group such as an alkyl group is a quite stable residue. This monosaccharide derivative is completely free of any residue harmful to the human body such as an aromatic residue. Therefore, the safety thereof is considerably high and the monosaccharide derivative can thus be incorporated into the diet of the foods and the beverages as well as pharmaceutical preparations.

In this connection, the substituent Y of the alpha-N-acetyl-glucosaminyl bond-containing monosaccharide derivative appearing in the chemical formula (1) may be a group having 1 to 27 carbon atoms and specific examples thereof include aliphatic hydrocarbon groups, for instance, straight or branched alkyl groups such as ethyl groups; and alicyclic alkyl groups represented by those derived from sterols, or steroid ring-containing groups such as cholestanyl groups. Similarly, the substituent Y may be a group having 1 to 27 carbon atoms and specific examples thereof having 3 carbon atoms include, for instance, straight acyl groups; branched acyl groups; and alicyclic acyl groups, for instance, sterol-derived group-containing acyl groups and steroid ring-containing acyl groups such as cholestanyl-containing acyl groups.

The cholestanyl group-containing monosaccharide derivative (GlcNAc-alpha-cholestanol) shows an *H. pylori*-proliferation inhibitory effect on the order of 40 to 50% at a concentration of not more than 180 µM in the experiments similar to those described above. This monosaccharide derivative also possesses characteristic properties similar to those observed for the derivative: GlcNAc-alpha-O-Et and it would be expected that this derivative likewise has safely although it is more or less lower than that observed for GlcNAc-alpha-O-Et.

These alpha-N-acetyl-glucosaminyl bond-containing monosaccharide derivatives are used as proliferation inhibitors of *H. pylori*. These saccharide derivatives may be used alone, a plurality of them may be used in combination or they may likewise be used in combination with a kind of proton pump-inhibitor such as Lansoprazole or Omeprazole and two kinds of antibiotics such as Amoxicillin and Clarithromycin.

This proliferation inhibitor of *H. pylori* may likewise be used as an additive for the diet of the foods and the beverages. In this respect, examples of such diet of the foods and the beverages may be foods, for instance, dairy products such as yoghurt; and beverages such as drink water, cocoa and juices. In this connection, it is preferred to incorporate the proliferation inhibitor of *H. pylori* into the diet of these foods and beverages in an amount ranging from 0.02 to 0.2%. It is more preferred that the diet of these foods and beverages are those continuously ingested. This is because the *H. pylori*-proliferation inhibitory effect may further be improved and the continuous ingestion thereof would thus inhibit the peptic diseases, for instance, gastric diseases such as chronic gastritis.

This proliferation inhibitor of *H. pylori* is used as an effective component to be incorporated into a pharmaceutical preparation. Such a pharmaceutical preparation may be in any form such as a tablet, a capsule, a granule, a pill, an emulsion, a powder, a syrup, a liquid preparation, or an injection. Such a pharmaceutical preparation may further comprise components for preparing each pharmaceutical preparation such as excipients, distilled water and physiological saline; and/or other medical components. It is more preferred that these pharmaceutical preparations should be taken once or continuously to thus improve the *H. pylori*-proliferation inhibitory effect and accordingly, the ingestion thereof would permit the curing or alleviation of the peptic diseases, for instance, gastric diseases such as chronic gastritis.

The following are the description of examples which relate to the preparation of alpha-N-acetyl-glucosaminyl bond-containing monosaccharide derivatives and the preparation of the proliferation inhibitor of *H. pylori* of the present invention.

PREPARATION EXAMPLE 1

Preparation of GlcNAc alpha-O-Et (1) Through Chemical Synthesis

Ethoxy 2-acetamide-2-deoxy-N-acetyl-alpha-D-glucosaminide (GlcNAc alpha-O-Et (1)) as an example of the alpha-N-acetyl-glucosaminyl bond-containing monosaccharide derivative represented by the foregoing chemical formula (1) to which the present invention is applied is detailed in this Preparation Example 1. This derivative can be synthesized according to the following chemical reaction scheme.

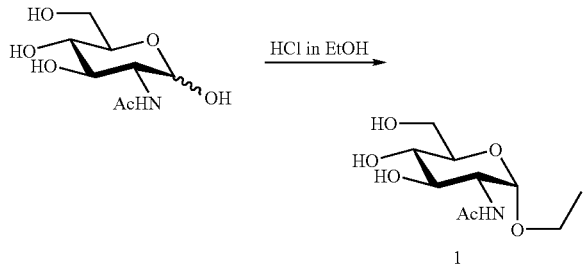

Specifically, 3.2864 g (14.86 mmol) of N-acetyl-D-glucosamine was added to a 200 ml volume eggplant-shaped flask containing HCl gas-bubbled EtOH (50.0 ml) to thus dissolve the compound into the latter, a tube packed with calcium chloride was attached to the flask and the resulting solution was then stirred at room temperature. Whether the reaction was completed or not was confirmed by the thin layer chromatography (TLC) technique (developer solvent: chloroform/methanol (3:1)). After the elapse of 85 hours, the reaction system was concentrated and as a result, pink-colored crystals were precipitated. A small amount of the resulting crystals was subjected to the thin layer chromatography (developer solvent: chloroform/methanol (3:1)), followed by the color development with iodine for 12 hours. The crystals were purified according to the column chromatography (developer solvent: chloroform/methanol (3:1)) to thus give a white crystalline product (alpha-derivative) in a yield of 75%. The identification of the resulting product was carried out according to the nuclear magnetic resonance (NMR) spectrometry technique (600 MHz).

$^1$H-NMR (600 MHz, CDCl$_3$): δ(ppm): 1.06(3H, t, J=7.6 Hz, —CH$_2$CH$_3$), 1.90(3H, s, CH$_3$CO), 3.34(1H, t, J=9.6 Hz, H-4), 3.35-3.41(1H, m, H-5), 3.57-3.66(4H, m, H-2, H-3, Ha-6, —CHaCHbH$_3$), 3.72(1H, dd, J=1.4 Hz, J=8.3 Hz, —CHaCHbH$_3$), 3.77(1H, dd, J=2.5 Hz, J=10.3 Hz, Hb-6), 4.73(1H, d, J=4.2 Hz, H-1)

$^{13}$C-NMR (150 MHz, CDCl$_3$): δ(ppm): 14.67(—CH$_2$CH$_3$), 22.51(CH$_3$CO), 54.29(C-2), 61.21(—CH$_2$CH$_3$), 64.58 (C-6), 70.69(C-5), 71.77(C-3), 72.39(C-4), 97.29(C-1), 175.08(CH$_3$CO).

These spectroscopic data clearly support the fact that the resulting product is GlcNAc alpha-O-Et (1).

(Confirmation of *H. pylori*-Proliferation Inhibitory Effect of Compound 1 (GlcNAc alpha-O-Et (1)))

The effect of GlcNAc alpha-O-Et on *H. pylori* was confirmed according to the following procedures. Bacterial cells of *H. pylori* (ATCC 43504) stored in a brucella broth culture medium frozen at −80° C. were cultured in the same culture medium (3 mL) supplemented with 10% equine serum at 35° C. in the presence of 15% CO$_2$ for 40 hours according to the shaking culture technique, the movement of bacterial cells was observed under a microscope and non-coccoid type bacterial cells of *H. pylori* were recovered. The culture medium was inspected for the OD values at 600 nm, followed by the dilution thereof with Muller-Hinton culture medium supplemented with 5.5% equine serum such that the number of bacterial cells present therein was equal to 4×10$^7$, and 3 mL thereof in total was cultured at 35° C. in the presence of 15% CO$_2$ for 24 hours according to the shaking culture technique, followed by the confirmation by a microscope to thus give an *H. pylori*-containing culture medium (bacterial cell density: 2×10$^7$/mL) used in the test for the confirmation of the effect of the foregoing compound. On the other hand, there were prepared Muller-Hinton culture mediums (free of any bacterial cell of *H. pylori*) each containing 902.6 μM to 14.4 mM of the foregoing GlcNAc alpha-O-Et and supplemented with 5% equine serum, each of the resulting culture mediums was added to the foregoing *H. pylori*-containing culture medium in a mixing ratio of 1:1 (by volume) (total volume: 100 μL each; on a 96-well plate), followed by the mixing thereof and the subsequent cultivation at 35° C. in the presence of 15% CO$_2$ for 96 hours. After the cultivation thereof over a predetermined period of time, the bacterial cell density thus proliferated was determined by the determination of the OD values at 600 nm, followed by the comparison of the result observed for the sample to which the candidate compound was added with that observed for the negative control free of any candidate compound (the control depicted in FIG. 1) to thus evaluate the proliferation inhibitory effect of the compound. In this respect, 1 U herein means 2.9 μmol/mL.

The results obtained using GlcNAc alpha-O-Et are plotted on FIG. 1.

As is clear from the data shown in FIG. 1, when adding GlcNAc alpha-O-Et in an amount of not less than 625 mU/mL (1.8 mM), it is confirmed that not less than 50% of the *H. pylori* proliferation is inhibited by the action of the compound.

PREPARATION EXAMPLE 2

Preparation of GlcNAc Alpha-Cholestanol (2) Through Chemical Synthesis

A compound: 3-beta-cholestanyl-2-acetamide-3,4,6-tri-O-benzyl-2-deoxy-alpha-D-glucosaminide (GlcNAc alpha-cholestanol (2)) as an example of the alpha-N-acetyl-glucosaminyl bond-containing monosaccharide derivative represented by the foregoing chemical formula (1) to which the present invention is applied is detailed in this Preparation Example 2. This derivative can be synthesized according to the following chemical reaction scheme.

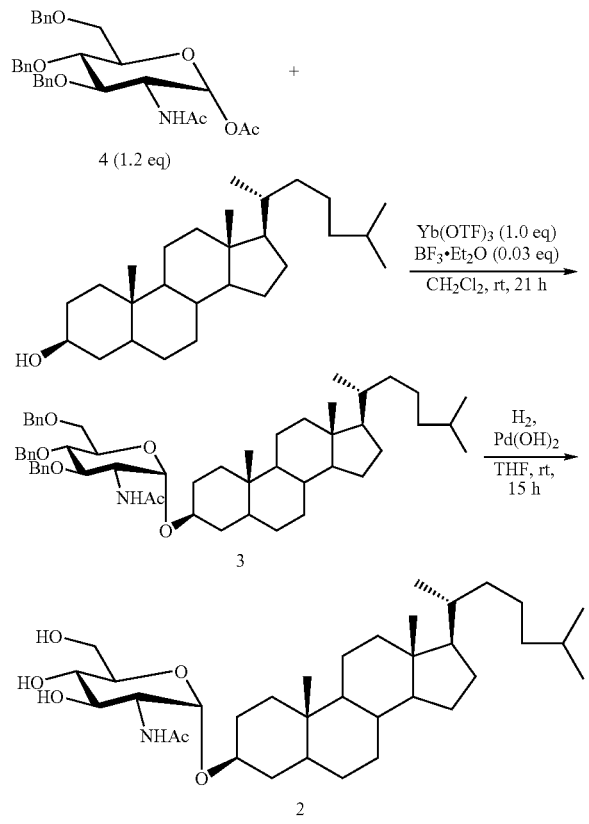

2-1. Synthesis of 3-beta-Cholestanyl-2-Acetamide-3,4,6-Tri-O-Benzyl-2-Deoxy-alpha-D-Glucosaminide (3) as Intermediate of GlcNAc Alpha-Cholestanol To a 20 ml volume 2-necked flask, Yb(OTf)$_3$ (129 mg, 0.2080 mmol) dried under reduced pressure for 6 hours in an oil bath maintained at 185° C. was added and then 0.5 ml of CH$_2$Cl$_2$ was added thereto in an Ar gas atmosphere. To the resulting mixture, a solution of glycosyl acetate (4) (133.2 mg, 0.2496 mmol) and 3-beta-cholestanol (80.8 mg, 0.2080 mmol) dissolved in CH$_2$Cl$_2$ was added, and 0.1M solution of BF$_3$·Et$_2$O (62 µl, 6.24 µmol) prepared in a messflask was then added to the mixture. The resulting mixture was stirred at room temperature for 21 hours, the progress of the reaction was confirmed according to the thin layer chromatography technique (developer solvent: hexane/AcOEt=1:2) and then the reaction was stopped by the addition of a saturated NaHCO$_3$ solution. The reaction system was extracted with a CH$_2$Cl$_2$/AcOEt mixed solvent, the resulting organic phase was washed with a common salt solution and then dried over Na$_2$SO$_4$. Subsequently, the organic phase was filtered and then concentrated to thus give unpurified crystals. The unpurified product was purified according to the preparative thin layer chromatography technique (developer solvent: benzene/AcOEt=5:1) to thus obtain a glycoside derivative mixture in a yield of 70% (alpha/beta ratio=23/77; yield of alpha-derivative (3): 16.1%).

The following are the spectrometric data of the alpha-derivative thus isolated obtained by the use of $^1$H-NMR and $^{13}$C-NMR spectrometers (available from JEOL Ltd.), and these data clearly indicate that the derivative has the structure specified above as that for the compound (3).

$^1$H-NMR (600 MHz, CDCl$_3$): δ(ppm): 1.86(3H, s, H-8), 0.57-1.97(47H, m, 3-beta-cholestanyl), 3.50(1H, tt, J=5.4 Hz, J=10.9 Hz, H-1'), 3.68(1H, t, J=9.5 Hz, H-3), 3.67(1H, dd, J=1.9 Hz, J=10.9 Hz, H-6$_a$), 3.72(1H, t, J=9.3 Hz, H-4), 3.76(1H, dd, J=4.3 Hz, J=8.8 Hz, H-6$_b$), 3.89(1H, ddd, J=1.9 Hz, J=4.1 Hz, J=9.4 Hz, H-5), 4.24(1H, td, J=3.8 Hz, J=9.8 Hz, H-2), 4.91(1H, d, J=3.8 Hz, H-1), 5.32(1H, d, J=9.3 Hz, —NHAc), 4.50-4.85(6H, m, —OC$\underline{H}_2$Ph), 7.16-7.35(15H, m, —OC$\underline{H}_2$Ph);

$^{13}$C-NMR (150 MHz, CDCl$_3$): δ(ppm): 23.48(C-8), 12.07-56.44(3-beta-cholestanyl), 52.54(C-2), 68.74(C-6), 70.93(C-5), 76.98(C-1'), 78.50(C-4), 80.82(C-3), 96.16(C-1'), 169.62(C-7), 70.40-75.03(—OC$\underline{H}_2$Ph), 127.59-128.51(—OCH$_2$C($\underline{CHCH}$)$_2$CH), 138.10-138.57(—OCH$_2$$\underline{C}$(CHCH)$_2$CH)

2-2. Synthesis of 3-beta-Cholestanyl-2-Acetamide-2-Deoxy-N-Acetyl-alpha-D-Glucosaminide (GlcNAc alpha-Cholestanol (2))

To a 20 ml volume 2-necked, eggplant-shaped flask containing 3 ml of THF, 32.1 mg (0.037 mM) of the alpha-D-glucosaminide (3) prepared above was added and dissolved to THF, followed by the addition of 54.7 mg (0.39 mmol) of palladium hydroxide and the stirring of the resulting mixture at room temperature while bubbling the mixture with hydrogen gas. The progress of the reaction was confirmed according to the thin layer chromatography technique (developer solvent: chloroform/methanol (5:1)). After the elapse of 15 hours, the palladium hydroxide was filtered off from the reaction mixture, the resulting filtrate was purified according to the silica gel column chromatography technique (developer solvent: chloroform/methanol (5:1)) to thus obtain a white crystalline product. The resulting product was analyzed by the $^1$H-NMR spectrometry and accordingly, the results thus obtained clearly supported the fact that the product had the foregoing structure represented by the compound 2.

$^1$H-NMR (600 MHz, CDCl$_3$): δ(ppm): 0.68-1.85(3-beta-cholestanyl), 2.15(3-beta-cholestanyl), 3.52-3.57(3-beta-cholestanyl), 1.97(3H, s, CH$_3$CO), 3.63-3.68(4H, m, H-3, H-4, H-5, Ha-6), 3.78-3.84(2H, m, H-2, Hb-6), 4.93(1H, d, J=3.4 Hz, H-1).

Confirmation of *H. pylori*-Proliferation Inhibitory Effect of Compound 2 (GlcNAc alpha-Cholestanol (2))

The effect of GlcNAc alpha-cholestanol on *H. pylori* was confirmed according to the following procedures. Bacterial cells of *H. pylori* (ATCC 43504) stored in a brucella broth culture medium frozen at −80° C. were cultured in the same culture medium (3 mL) supplemented with 10% equine serum at 35° C. in the presence of 15% CO$_2$ for 40 hours according to the shaking culture technique, the movement or behavior of bacterial cells was observed under a microscope and non-coccoid type bacterial cells of *H. pylori* were recovered. The culture medium was inspected for the OD values at 600 nm, followed by the dilution thereof with Muller-Hinton culture medium supplemented with 5.5% equine serum such that the number of bacterial cells present therein was equal to 4×10$^7$, and 3 mL thereof in total was cultured at 35° C. in the presence of 15% CO$_2$ for 24 hours according to the shaking culture technique, followed by the confirmation of the movement or behavior of bacterial cells by a microscope to thus give an H. pylori-containing culture medium (bacterial cell density: $2\times10^7$/mL) used in the test for the confirmation of the effect of the foregoing compound. On the other hand, there were prepared Muller-Hinton culture mediums (free of any bacterial cell of H. pylori) each containing 45 μM to 360 μM of the foregoing GlcNAc alpha-cholestanol and supplemented with 5% equine serum, each of the resulting culture mediums was added to the foregoing H. pylori-containing culture medium in a mixing ratio of 1:1 (by volume) (total volume: 100 μL each; on a 96-well plate), followed by the mixing thereof and the subsequent cultivation at 35° C. in the presence of 15% $CO_2$ for 96 hours. After the cultivation thereof over a predetermined period of time, the bacterial cell density thus proliferated was determined by the measurement of the OD values at 600 nm, followed by the comparison of the result observed for the sample to which the candidate compound was added with that observed for the negative control free of any candidate compound (the control depicted in FIG. 2) to thus evaluate the proliferation inhibitory effect of the compound. In this respect, 1 U herein means 2.9 μmol/mL. In this connection, the foregoing GlcNAc alpha-cholestanol is never dissolved simply in the culture medium in such a high concentration. Accordingly, the insoluble fraction included in the resulting solution was removed, in advance, through filtration. For this reason, the foregoing concentrations are all expressed in terms of the concentrations of the compounds while assuming the complete dissolution thereof in the culture medium and therefore, the practical concentrations are lower than those indicated or specified above.

Figure 2:
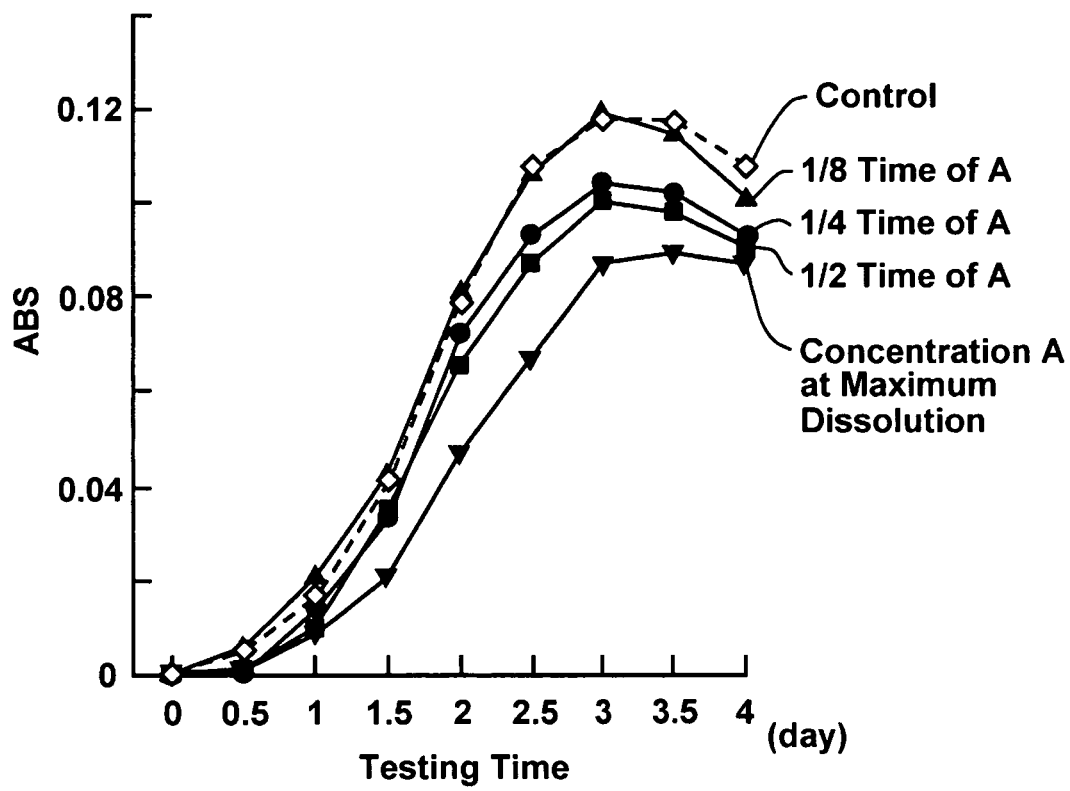
FIG. 2 is a graph showing the *H. pylori*-resistant effect of an proliferation inhibitor of *H. pylori* comprising alpha-N-acetyl-glucosaminyl bond-containing monosaccharide derivative (Compound 2) to which the present invention is applied.

The results obtained using GlcNAc alpha-cholestanol are plotted on FIG. 2. The concentration of a solution obtained by dissolving the compound in an amount as large as possible was referred to as the concentration A. As a result, it was confirmed that the use of the compound in an amount of at least 62.5 mU/mL (180 μM) permitted the inhibition of about 40 to 50% of the proliferation of H. pylori (within 1.5 to 2 days).

INDUSTRIAL APPLICABILITY

The alpha-N-acetyl-glucosaminyl bond-containing monosaccharide derivative shows its antibacterial effect against H. pylori in such a mechanism that it can inhibit all kinds of proliferative activities essential or indispensable to the growth of the bacterial cells, completely unlike the conventional antibiotics and therefore, it is quite useful as an effective component of an H. pylori-resistant agent.

The proliferation inhibitors of H. pylori comprising these sugar derivatives are effective components for pharmaceutical preparations as well as additives for supplements, the diet of the foods and the beverages.

The diet of the foods and the beverages each comprising the proliferation inhibitors of H. pylori are useful as functional foods and beverages as well as health foods and beverages. The pharmaceutical preparation comprising the proliferation inhibitors of H. pylori is accordingly useful for curing, alleviation and/or prevention of gastric diseases such as chronic gastritis and gastric ulcers, and peptic diseases, which are caused by the bacterial cells of H. pylori.

What is claimed is:

1. A method for direct inhibition of proliferation of *Helicobacter pylori* in a human stomach comprising:
   administering orally to a subject infected with *Helicobacter pylori* an effective amount for the direct inhibition of *Helicobacter pylori* in the human stomach of a food product, a beverage product, a supplement, or a pharmaceutical preparation comprising an alpha-N-acetyl-glucosaminyl bond-containing monosaccharide represented by the following chemical formula (1)

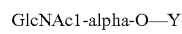

GlcNAc1-alpha-O—Y    (1)

wherein in the formula (1), Y is: a straight-, branched- or cyclic- aliphatic hydrocarbon group having 1 to 27 carbon atoms; or a straight-, branched- or cyclic-acyl group having 1 to 27 carbon atoms.

2. The method according to claim 1, wherein the subject infected with *Helicobacter pylori* is a patient with gastric disease, wherein the gastric disease includes chronic gastritis, peptic ulcers, gastric cancers and/or gastric malignant lymphoma.

* * * * *